United States Patent [19]

Goldberg et al.

[11] Patent Number: 4,819,617
[45] Date of Patent: Apr. 11, 1989

[54] VISCOELASTIC MATERIAL FOR OPHTHALMIC SURGERY

[75] Inventors: Eugene P. Goldberg, Gainesville; A. Jayakrishnan, Kerala, both of Fla.

[73] Assignee: University of Florida, Gainesville, Fla.

[21] Appl. No.: 903,445

[22] Filed: Sep. 4, 1986

[51] Int. Cl.$^4$ ............................................. A61B 19/00
[52] U.S. Cl. ................................ 128/897; 514/912; 536/98; 623/6
[58] Field of Search ................. 128/1 R, 303 R, 305; 514/912, 914, 915, 913; 604/891, 892, 893; 623/4, 5, 6; 536/56, 63, 98

[56] References Cited

U.S. PATENT DOCUMENTS

| | | | |
|---|---|---|---|
| 4,141,975 | 2/1979 | Gay et al. | 514/129 |
| 4,382,953 | 5/1983 | Ishii et al. | 514/912 |
| 4,407,792 | 10/1983 | Schoenwald et al. | 514/912 |
| 4,421,748 | 12/1983 | Trager et al. | 514/912 |
| 4,510,145 | 4/1985 | Schacher | 514/415 |

FOREIGN PATENT DOCUMENTS 2169508  7/1986  United Kingdom ................ 514/915

OTHER PUBLICATIONS

Fechner, "Methylcellulose in Lens Implantation", J. of Amer. Intraocular Society, vol. 3, (1977), pp. 180–181.
Klug, Encyclopedia of Polymer and Science Tech., vol. 3, (1965), pp. 520–539.
Remington's Pharmaceutical Sciences, 15th Ed., Editor: Arthur Osol, Mack Pub., (1975), pp. 1243–1244.
Wilhelmus et al., "Pseudovitreous Fluid Based on Sodium Carboxymethylcellulose", Annals of Ophthalmology, Apr. 1984, pp. 350–352.

*Primary Examiner*—Richard J. Apley
*Assistant Examiner*—Paul B. Prebilic
*Attorney, Agent, or Firm*—Dennis P. Clarke

[57] ABSTRACT

The present invention embodies a composition particularly adapted for use as an ophthalmic viscosurgical material for use in the anterior chamber of the eye consisting essentially of an aqueous solution preferably having a near physiological pH and osmolarity and containing at least about 1.5%, by weight, of a water soluble physiologically acceptable derivative of carboxymethylcellulose having a molecular weight greater than 500,000 and a degree of substitution (DS) greater than about 0.4, the aqueous solution having a viscosity greater than about 10,000 centipoises.

The invention further embodies an improved ophthalmic viscosurgical procedure wherein the anterior chamber of the eye is filled with a space-filling corneal endothelium and ocular tissue protective surgical material, the improvement comprising the utilization of an ophthalmic surgical material having the above described composition.

17 Claims, No Drawings

VISCOELASTIC MATERIAL FOR OPHTHALMIC SURGERY

BACKGROUND OF THE INVENTION

1. Field of the Invention

The present invention relates to novel viscoelastic viscosurgical materials and ophthalmic surgical techniques utilizing the materials.

2. Prior Art

In ophthalmic surgical procedures such as intraocular lens implantation, cataract surgery, retinal detachment repair, etc., there exists a need for viscous, gel-like compositions to fill the chambers of the eye to protect sensitive tissue such as the corneal endothelium from trauma. See U.S. Pat. No. 4,141,975; Pruett et al, Arch. Ophthalmol., 97:2325 (1979); Holmberg et al, Ophthalmology, 91:45 and 53 (1984); Pape et al, Ophthalmology, 87:669 (1980); MacRae et al, Am. J. Ophthalmol., 95:332 (1983); and Miller et al, Annals Ophthalmol., 13:811 (1981).

The most commonly employed materials are solutions of hyaluronic acid (HA), chondroitin sulfate (CS) and methylcellulose (MS). HA has been the most widely used and appears to owe its unusual rheological and viscoelastic solution properties to its polyanion polyelectrolyte molecular structure.

However, HA is extremely expensive. Furthermore, it requires extraordinary purification to remove as much proteinaceous immunogenic material as possible but still may provoke immune reactions in some patients. Its use is also often accompanied by significant undesirable intraocular pressure rise which necessitates washing HA from the eye at the end of surgery and may also require antiglaucoma therapy.

It has also been suggested to employ a solution of a relatively low molecular weight (i.e., 350,000) sodium carboxymethylcellulose as a "pseudovitreous fluid" in the posterior chamber [Wilhelmus et al, Annals of Ophthalmology, 16:350-352 (1984)]. In addition, Penkov et al [Oftalinol. Zh (USSR), 1984(4):215-217] discloses that 0.5% solutions of sodium carboxymethylcellulose may be used as a space filler in the eye.

It is an object of the present invention to provide improved ophthalmic viscoelastic surgical materials and ophthalmic surgical techniques embodying same which are not subject to the above-noted disadvantages.

SUMMARY OF THE INVENTION

The present invention embodies a composition particularly adapted for use as an ophthalmic viscosurgical material for use in the anterior chamber of the eye consisting essentially of an aqueous solution preferably having a near physiological pH and osmolarity and containing at least about 1.5%, by weight, of a water soluble physiologically acceptable derivative of carboxymethylcellulose having a molecular weight greater than 500,000 and a degree of substitution (DS) greater than about 0.4, the aqueous solution having a viscosity greater than about 10,000 centipoises.

The invention further embodies an improved ophthalmic viscosurgical procedure wherein the anterior chamber of the eye is filled with a space-filling corneal endothelium and ocular tissue protective surgical material, the improvement comprising the utilization of an ophthalmic surgical material having the above described composition.

DETAILED DESCRIPTION OF THE INVENTION

The below-listed terms are employed throughout the specification and claims and they are defined as follows:

(1) "Viscoelastic" material refers to certain viscous solutions or compositions having the requisite viscous gel-like properties which enable their use to fill the anterior chamber of the eye.

(2) "Viscosurgical" material or technique refers to the viscoelastic surgical materials inserted in the eye or the surgical techniques employed to fill the anterior chamber of the eye during cataract, lens implant, etc., surgeries.

(3) "CMC" as used herein refers to any water soluble physiologically acceptable derivative, of carboxymethylcellulose, e.g., sodium carboxymethyl-cellulose.

(4) "Physiologically acceptable" is employed to refer to materials which, when in contact with tissues in the body, are not harmful thereto. For example, the term is used to define the media in which the CMC is dissolved to form the viscoelastic material. The term is intended in this context to define aqueous solutions which are approximately isomolar with the physiological environment of the eye. Generally such media have an osmolarity of the order of 250–300 and are buffered to maintain a pH of from about 7.0 to 7.5.

The present invention is predicated on the discovery that solutions of physiologically acceptable carboxymethylcellulose derivatives (CMC) having the molecular weight, DS, concentrations and viscosities set forth above are unexpectedly superior to solutions of CMC having properties outside these critical ranges when employed as ophthalmic viscosurgical materials in the anterior chamber of the eye both as a viscoelastic space filler and protector for the surrounding sensitive tissue therein during intraocular surgery.

Wilhelmus, supra, discloses the use of CMC as a pseudo-vitreous material and suggests its applicability as a bioacceptable vitreous replacement. However, because of the very different physiological environment of the anterior chamber (A.C.) as compared with the vitreous posterior chamber, those skilled in the art would not conclude from the disclosure of Wilhelmus that CMC would be acceptable in the A.C. Wilhelmus, moreover, does not suggest that CMC might be used as a tissue protector in cataract surgery, etc. The A.C. is a different, more reactive physiological environment than the posterior chamber (P.C.) from the standpoint of biocompatibility. The U.S. Food and Drug Administration, for example, recognizes this important difference in that it requires that implant materials for use in the A.C. be tested in the A.C. and similarly that P.C. implants require P.C. evaluation. Acceptable biocompatibility in the P.C., therefore, does not imply safe use and effectiveness for A.C. applications.

The use by Wilhelmus of a 350,000 molecule weight CMC in the P.C. is not suggestive of the critical importance in the use of a higher molecular weight material for a viscosurgical device material in the anterior chamber of the eye. It is critically essential to the present invention to use CMC having molecular weights substantially higher than 350,000 and a D.S. greater than about 0.4%.

The Penkov et al, supra, disclosure of 0.5% as an optimum concentration for solutions of CMC as a space-filler in the A.C. evidences the lack of realization by the authors of the requirements for CMC solutions when used in ophthalmic surgeries. It is critically essential to the invention to use CMC solutions having concentrations no lower than 1.5%, by weight, and viscosities no lower than about 10,000 centipoise in order to obtain the balance of properties required of a practical viscosurgical material in the A.C., i.e.:

(a) Readily injectable with non-Newtonian viscosity (shear thinning);

(b) Gel-like high viscosity at low shear ($>10,000$ cps) to insure no loss by leakage through wound opening and to enable gentle tissue manipulation;

(c) Lubricating and non-adhesive protection of endothelium, iris and other tissue from contact with the implant and instruments;

(d) Easily irrigated out of the A.C. after surgery;

(e) No significant inflammatory response or increase in intraocular pressure (IOP) with use; and (f) Rapid clearance ($<1$ week) from the eye of residual material.

The compositions of the invention exhibit excellent shear dependent viscous properties, maintain the anterior chamber, and are easy to inject, manipulate and visualize. Tests have shown the material to be non-pyrogenic, non-toxic and non-immunogenic.

Carboxymethylcellulose is an anionic polysaccharide with the following typical repeat unit structure for a compound with a degree of substitution of 1.0 (one carboxymethyl group per anhydroglucose ring):

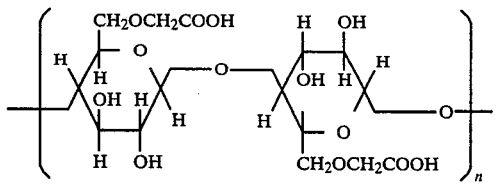

CMC, as the sodium salt, for example, is prepared by carboxymethylation of alkali cellulose with sodium monochloracetate. Anhydroglucose ring structures ($\beta$-glucopyranose residues) repeat in the polymer unit structure and are joined by 1,4-glucoside linkages. CMC (sodium salt) is commercially available as the sodium salt in various molecular weights and various degrees of substitution (carboxymethylation).

CMC is not a single, simple compound although the basic chemical structure of carboxymethylcellulose may be depicted as above. The degree of substitution (DS) may vary from below 0.4 carboxymethyl groups per anhydroglucose unit to a theoretical maximum of 3.0. Both DS and molecular weight are critical parameters in defining the viscoelastic properties of the CMC solutions for use in the anterior chamber of the eye. Generally, the higher the DS and the higher the molecular weight, the greater the viscosity of a solution of the CMC.

It is critical to the present invention that CMC having a MW greater than 500,000 and a DS greater than 0.4 be used. It is essential to use a high MW (greater than 500,000) and $>0.4$ DS to produce very viscous solutions (i.e., $>10,000$ cps) at low CMC concentrations (i.e. $>1.5\%$, by weight) with suitable osmolarity for surgical applications (250-300 m osmolar). It is also preferred to employ a degree of substitution greater than 0.4. Although MW and DS may be varied as well as solution concentrations to produce various viscoelastic solution properties, CMC solutions of 2.2% to 4.2% were shown to perform excellently in intraocular implant surgery with good tissue protection and with little rise in intraocular pressure; prepared from a CMC having a MW of 700,000–900,000, DS ~0.8 in sufficient saline buffer to adjust osmolarity and pH to a physiological level. A 2.2% CMC solution exhibited a viscosity of about 20,000 cps and anterior chamber injections of 0.1 ml in rabbit eyes showed no adverse behavior. Surgical intraocular lens implant trials in rabbits by several ophthalmic surgeons using solutions of 2.2 to 3.5% CMC of the above molecular weight and DS indicated excellent surgical properties comparable to commercial hyaluronic acid solutions.

A water soluble, physiologically acceptable derivative of carboxymethycellulose may be employed. It is preferred to employ salts of carboxymethylcellulose such as alkali metal salts, e.g., sodium carboxymethylcellulose, in the practice of the invention.

The CMC may be dissolved in any physiologically acceptable solution having a physiologically acceptable pH and osmolarity, such as saline or buffered saline.

It is essential that the CMC have a MW above about 500,000. There is no practical upper limit for the MW so long as the ultimate solution has the concentration of CMC and viscosity specified above.

The upper limit as to concentration will depend, of course, upon the MW and DS of the CMC and the necessity for a viscosity thereof greater than about 10,000 centipoises. Generally, an upper limit of about 5%, by weight, is practical. Preferably, concentrations of 2.0 to 4.5 weight % provide optimum results.

It will be understood by those skilled in the art that by "ophthalmic surgical or surgery" is meant any intraocular surgery such as intraocular lens implantation, cataract surgery, corneal transplant surgery, glaucoma surgery, retinal detachment repair, etc. The composition of the invention is suitable for utilization in any of these ophthalmic surgical techniques.

An important advantage associated with the use of CMC is that, unlike hyaluronic acid or chondrotin sulfate, it is not derived from a proteinaceous source and has virtually no protein associated therewith. Accordingly, the use of CMC does not involve the danger of foreign protein induced immunogenic activity and does not require the extensive and costly purification procedures required for HA and COS.

It should be noted that purification of the CMC solution by filtration through filters as small as 0.2 micron has some effect upon reducing the apparent viscosity at a given concentration even though the molecular weight remains unchanged. This is apparently due to changes in the solution gel structure. Additionally, if sterilization is by autoclaving under typical autoclave conditions of 120° for 15 minutes there may be a reduction in solution viscosity. For example, a solution of 3.3% concentration and 75,000 cps viscosity may be used to achieve a nominal 45,000 cps viscosity after ultrafiltration and autoclave sterilization.

In several in vivo evaluations, a 4.2% solution of CMC (sodium salt, Hercules Co., 7H3SF) which yields a post-filtration and post-autoclave viscosity of about 58,000 cps has been used for intraocular pressure and biocompatibility studies in rabbits and cynomolgus monkeys with excellent results (see Examples hereinafter). This material has a slightly higher viscosity than the HA in current clinical use (Ca. 40,000 cps). Other studies were done with 3.3% CMC solutions having a post-purification, post-sterilization viscosity of 45,000 cps. For the purposes of the present invention, a viscosity greater than about 10,000 cps and a CMC concentration greater than about 1.5 weight % is required, in that lower viscosities will not maintain the A.C. very well, will leak, will clear from the A.C. too rapidly, will not afford adequate tissue protection, and will not move tissue well. Extremely high viscosities are limited only by being more difficult to inject and more difficult to irrigate. [All viscosities herein are determined using a Brookfield LVTD viscometer at 6 rpm and 23° C. using spindle #4 and silicone oil as a standard calibration.]

The critical CMC compositions of the invention are "non-Newtonian" in their rheological (flow) properties or "pseudoplastic" in behavior, i.e., they become less viscous with increasing shear. Thus, if a solution of high viscosity CMC appears to be a viscous syrup as it is poured from a bottle, it will behave as a less viscous liquid when applied as a lotion, and when high shear stress is removed it will revert to its original more viscous state. This type of flow behavior is referred to as pseudoplasticity or time-independent shear-thinning—a form of non-Newtonian flow. In viscosity measurements, such materials are extremely sensitive to viscometer geometry and the rotational speed of the viscometer (shear rate). The viscosity of polyelectrolytes such as CMC are also extremely sensitive to temperature, concentration and molecular weight.

Another important property of CMC which is a polyanionic polyelectrolyte, is its stability to polyvalent cations. Specifically, it will not form crosslinked gels in contact with divalent cations such as calcium. Since calcium ion is normally present in the physiological environment, the stability of CMC in the indicated preferred ranges of composition to calcium ion is an important property.

Biocompatibility studies in rabbits and cynomolgus monkeys were conducted as follows:

EXAMPLE 1

Healthy NZW rabbits (2.5–3.5 kg) were selected for the study. All rabbits were subjected to a biomicroscopic slit lamp exam (SLE) prior to surgery. Only those with no anterior segment abnormalities were used. They were followed for one week after A.C. injection. Each rabbit was individually housed with cage identity cards for identification purposes. The rabbits were given standard food and water adlibitum during the course of the study.

The test material was injected in the A.C. of rabbit eyes to evaluate post-operative biocompatibility of the test material in direct contact with living ocular tissues. Placement in the A.C. facilitates microscopic (SLE) evaluation of any tissue reactions as well as direct viewing of the viscoelastic material throughout the period of the study.

Controls consisted of a similar procedure using BSS (Alcon) in the opposite eye of the same rabbit. Each animal was weighed and sexed prior to surgery.

The surgical procedure described below was followed:
1. General anesthesia was induced by 20 mg/kg ketamine hydrochloride (Ketaset, 100 mg/ml, Bristol U.S.A.) and 4 mg/kg xylazine (Rompun, 20 mg/ml Haver-Lockhart, U.S.A.) injected I.M.
2. SLE exam of the anterior segment.
3. Tetracaine (0.5% eye drops) applied to the eye to anesthetize the cornea.
4. Inserted a wire speculum.
5. Penetrated into the A.C. with a 25 g or smaller needle at the corneo-limbal junction.
6. Aspirated 0.1–0.2 of aqueous humor.
7. Injected 0.1 cc of viscoelastic material through the same penetration site.
8. Applied 1% cyclopentolate hydrochloride (Cyclogyl, Alcon, U.S.A.).

A 3.3%, by weight, solution of Na-CMC in buffered saline, having a post-filtration and post-autoclave sterilization viscosity of about 45,000 cps, was tested in rabbits as described above.

In 9 New Zealand White rabbits (9 experimental, 9 control-BSS eyes), the anterior chamber of an eye was evacuated and the chamber re-filled with the 3.3% viscoelastic solution as described above.

The nine experimental animals exhibited mild inflammation of the eyes which subsided in 24 hours. The experimentally tested eyes compared well with the control eyes and no increase in intraocular pressure was observed in any of the animals.

EXAMPLE 2

The above procedures were repeated in 6 cynomolgus monkeys (6 experimental and 6 BSS control eyes) with a 4.2% solution of CMC. The monkeys were monitored at 2, 4, 6 and 8 hours and 1, 2, 3, 7 and 14 days.

A Na-CMC (DS:0.8; average molec. wt. 700,000–900,000) was dissolved in buffered saline (pH 7.0–7.5) to produce a solution containing 4.2%, by weight, of Na—CMC having a post-filtration and post-autoclave sterilization viscosity of about 58,000 cps. This solution was tested in cynomolgus monkeys as described above.

Slit lamp examinations (SLE) were conducted approximately 4 hours, 24 hours, 48 hours, 72 hours, one week and two weeks after the procedure. Ocular changes are described, or scored according to the system of McDonald and Shaddock.

Tonometry by using Schiotz tonometer were carried out just before the procedure, and at 2, 4, 6, 8 and 24 hours and daily thereafter. When IOP was normal for 3 consecutive days, then IOP was measured every 2 days thereafter to end of study (2 weeks) after anesthetizing with intramuscular injection of Ketaset. Photos were taken at 24 hours, 72 hours, one week and two weeks after the procedure. After the last examination the eyes were enucleated and subjected to histopathology.

For each post-op SLE, a complete evaluation chart was recorded. Clinical evaluations were carried out by scoring or commenting on the chart. Corneal edema and inflammatory response were scored 0 to 4 according to severity. The degree of severity was thus assessed.

The IOP results are set forth in Table 1.

TABLE 1

| Intraocular Pressure (IOP) In Cynomolgus Monkeys After Injection* | |
|---|---|
| Time | IOP (mmHg)** |
| Pre-op | 16 |
| 2 hr. | 31 |
| 4 hr. | 34 |
| 6 hr. | 35 |
| 8 hr. | 31 |
| Day-1 | 21 |
| Day-2 | 16 |
| Day-3 | 13 |
| Day-7 | 16 |

TABLE 1-continued

Intraocular Pressure (IOP) In
Cynomolgus Monkeys After Injection*

| Time | IOP (mmHg)** |
|---|---|
| Day-14 | 15 |

*Volume of Viscoelastic Solution 50% of A.C. Volume
**Average for 6 Animals.

All experimentally tested eyes gave evidence of transient, low grade inflammation which subsided after 3 days and the eyes remained clear thereafter. The transient increase in IOP returned to pre-operative normal level within 24 hours. Histopathology showed the appearance of a few clump cells and mononuclear inflammatory cells but no foreign body (F.B.) reaction.

EXAMPLE 3

Rabbit surgery trials by several ophthalmologists were carried out with iso-osmolar, pH 7, Na—CMC solutions containing 2.2–2.4% Na—CMC. Viscosities were determined using a Brookfield LVTD viscometer at 23° C. and 6 rpm using spindle #4 in a water jacketed chamber modified with a 13×100 mm test tube to reduce sample volume. These solutions had viscosities of about 20,000–27,000 cps (commercial samples of HA have viscosities of about 36,000 for these procedures). The solutions were used to maintain the A.C. in a typical A.C. intraocular lens implantation performed according to the following protocol:

IOL Implantations With ECLE—Rabbit A.C. IOL Implantation Using Na—CMC

1. General anesthesia induced by Ketaset 20 mg/kg and rompun 15 mg/kg given i.m.
2. SLE exam of the anterior segment.
3. Pentobarbital 65 mg/g through an i.v. E-Z set, with 27 g needle give as needed via the marginal ear vein.
4. Cyclogyl 1% and Neo-synephrine 2½% eye drops given several time to dilate the pupil, thus facilitating removal of the lens.
5. Insert a wire speculm.
6. Hemostasis and bleeder vessels cantery.
7. Penetration into the A.C. through a small corneal-scleral incision at the superior limbus.
8. Place 0.1 cc heparin into the A.C.
9. Use the irrigating cystotome to perform an anterior capsulatory.
10. Extend the incision.
11. Pull out the anterior capsule and clip off.
12. Express the nucleus.
13. Place temporary sutures and use the I/A machine to extract the cortex.
14. Remove temporary sutures.
15. Inject Na—CMC solution into A.C. to maintain chamber.
16. Inject Miochol (Acetylcholine 1:100, Cooper-Vision, U.S.A.) into the A.C. to constrict the pupil.
17. Slip the IOL into the A.C. and fit the haptics in the angle.
18. Center the lens.
19. Place saline into the A.C. and irrigate to flush CMC solution.
20. Close the wound with 10-0 prolene sutures.
21. Apply maxitrtol ointment (Neomycin 3.5 mg/g+polymyxin B 10,000 μ/g/ and dexamethasone 0.1% Alcon, U.S.A.) and cyclo gel eye drops (cyclopentolate 1% Alcon, U.S.A.) and cyclogyl eye drops (cyclopentolate 1% Alcon, U.S.A.). In case a more effective mydriasis is needed, apply Neo-synephrine 2½% (phenylephrine 2½% Winthrop, U.S.A.) or Atropine 1%.

Post-operative Follow-up

Each rabbit was examined regularly by SLE (slit lamp examination) post-op. No significant intraocular pressure rise was noted and after normal post-op inflammation, eyes became normal and quiet (within a few days).

The sodium CMC solutions performed adequately in handling, maintaining the anterior chamber and irrigation from the anterior chamber. Data for these samples are as follows:

A.
1. 2.4% CMC, Brookfield viscosity reading 35 (27,000 cps) osmolarity 296 M. osmol/kg.
2. 2.3% CMC, viscosity reading 31 (24,000 cps) 290 M. osmolar.
3. 2.2% CMC, viscosity reading 26 (20,000 cps) 274 M. osmolar.

All solutions had a pH of about 7.0.

The CMC derivatives of the present invention are miscible with hyaluronic acid (HA) and chondroitin sulfate (CS), the two most widely used anionic polysaccharides for ophthalmic surgical techniques.

It will be understood by those skilled in the art that the present invention includes compositions and ophthalmic surgical procedures wherein the CMC solutions contain other viscoelastic materials such as HA, CS, etc. Mixtures of CMC and other viscoelastic materials would have economic advantages over the use of HA and COS alone and would provide beneficial rheological and tissue protective properties.

EXAMPLE 4

Mixtures were prepared of the 3.3 wt % autoclave sterilized Na-CMC (D.S. ~0.8, mol. wt. ~800,000) described above with a sterile commercial sample of 1% Na-hyaluronic acid (Healon, Pharmacia Co.) in volume ratios of 2:1, 1:1 and 1:2, respectively. The two materials were miscible in all ratios and produced clear gel-like viscous-elastic solutions with properties suitable for use in ocular implant surgical techniques.

We claim:

1. A composition particularly adapted for use as an ophthalmic viscoelastic surgical material in the anterior chamber of the eye consisting essentially of an aqueous solution containing at least about 1.5%, by weight, of a physiologically acceptable, water-soluble carbomethylcellulose or salt thereof having a molecular weight greater than 500,000 and a DS of 0.4 to 3.0, said aqueous solution having a viscosity of about 10,000 to about 50,000 centipoises.

2. The composition of claim 1 containing a salt of carboxymethylcellulose.

3. The composition of claim 2 wherein said salt is an alkali metal salt of carboxymethylcellulose.

4. The composition of claim 3 wherein said salt is sodium carboxymethylcellulose.

5. The composition of claim 1 wherein said aqueous solution comprises a physiological saline solution of said carboxymethylcellulose or salt thereof.

6. The composition of claim 1 wherein said aqueous solution comprises a buffered physiological saline solution of said carboxymethylcellulose or salt thereof.

7. The composition of claim 1 wherein said carboxymethylcellulose or salt thereof has a molecular weight in the range of from about 500,000 to about 2,000,000.

8. The composition of claim 7 wherein said solution contains from about 1.5 to about 4.5% by weight of carboxymethylcellulose or salt thereof having a molecular weight of 500,000 to 1,000,000.

9. In an ophthalmic surgical procedure wherein the anterior chamber of the eye is filled with a viscoelastic space-filling and corneal endothelium protective surgical material, the improvement comprising the utilization as an ophthalmic surgical material a composition consisting essentially of an aqueous solution containing at least about 1.5%, by weight, of a physiologically acceptable, water-soluble carbomethylcellulose or salt thereof having a molecular weight greater than 500,000 and a DS of 0.4 to 3.0, said aqueous solution having a viscosity of about 10,000 to about 50,000 centipoises.

10. An ophthalmic surgical procedure according to claim 9 wherein said surgery comprises intraocular lens implantation.

11. An ophthalmic surgical procedure according to claim 9 wherein said surgery comprises cataract surgery.

12. An ophthalmic surgical procedure according to claim 9 wherein said surgery comprises a corneal transplant.

13. An ophthalmic surgical procedure according to claim 9 wherein said surgery comprises glaucoma surgery.

14. The composition of claim 1 additionally containing a different viscoelastic material miscible with said, carboxymethyl cellulose or salt thereof.

15. The composition of claim 14 wherein said different viscoelastic material is selected from the group consisting of hyaluronic acid and chondroitin sulfate.

16. An ophthalmic surgical procedure according to claim 9 wherein said ophthalmic surgical material additionally contains a different viscoelastic material miscible with said carboxymethylcellulose or salt thereof.

17. An ophthalmic surgical procedure according to claim 16 wherein said different viscoelastic material is selected from the group consisting of hyaluronic acid and chondroitin sulfate.

* * * * *

UNITED STATES PATENT AND TRADEMARK OFFICE
CERTIFICATE OF CORRECTION

PATENT NO.   : 4,819,617
DATED        : April 11, 1989
INVENTOR(S)  : EUGENE P. GOLDBERG; A. JAYAKRISHNAN; MOSHE YALON It is certified that error appears in the above-identified patent and that said Letters Patent is hereby corrected as shown below:

On the cover page, the inventors should be as follows:

--Eugene P. Goldberg, Gainesville, Fla.; A. Jayakrishnan, Kerala, India; Moshe Yalon, Gainesville, Florida--.

Signed and Sealed this

Ninth Day of January, 1990

*Attest:*

JEFFREY M. SAMUELS

*Attesting Officer*   *Acting Commissioner of Patents and Trademarks*